United States Patent [19]

Williams

[11] 4,090,299
[45] May 23, 1978

[54] ORTHODONTIC APPLIANCE

[76] Inventor: Richard E. Williams, 6284 Bullion Blvd., Las Vegas, Nev. 89103

[21] Appl. No.: 790,305

[22] Filed: Apr. 25, 1977

[51] Int. Cl.² ............................................ A61C 13/00
[52] U.S. Cl. ..................................................... 32/14 A
[58] Field of Search .................................. 32/14, 6, 7

[56] References Cited
U.S. PATENT DOCUMENTS

| 1,435,909 | 11/1922 | Arata ........................................... 32/7 |
| 1,797,481 | 3/1931 | Preston .............................. 32/14 E |
| 3,250,003 | 5/1966 | Collito ........................................ 32/6 |

Primary Examiner—Robert Peshock
Attorney, Agent, or Firm—Edgar W. Averill, Jr.

[57] ABSTRACT

An orthodontic appliance having an arcuate labial bar shaped to generally conform to the outer surface of a row of teeth and an arcuate lingual bar shaped for positioning on the inner surface of the same row of teeth. The two bars are held together and serve to urge the teeth located between the bars into a desired arcuate shape. Screw means are disclosed for attaching the labial and lingual bars and tapered screw means may be used whereby the further insertion of a tapered screw will tend to urge a tooth either away from or toward the center line of the jaw. The labial and lingual bars may be affixed to a collar or cap which may be attached to a molar or other tooth. A channel affixed to the lingual bar is disclosed whereby the nut for any screw may be held out of direct contact with the user's tongue. The labial and lingual bars may be attached by ratchet means located near the extremity of each bar.

3 Claims, 9 Drawing Figures

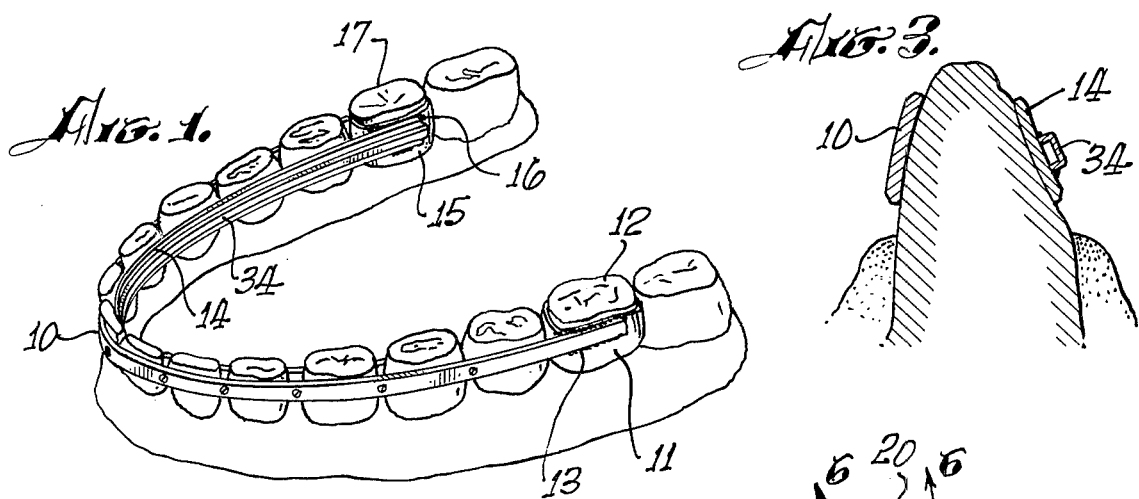
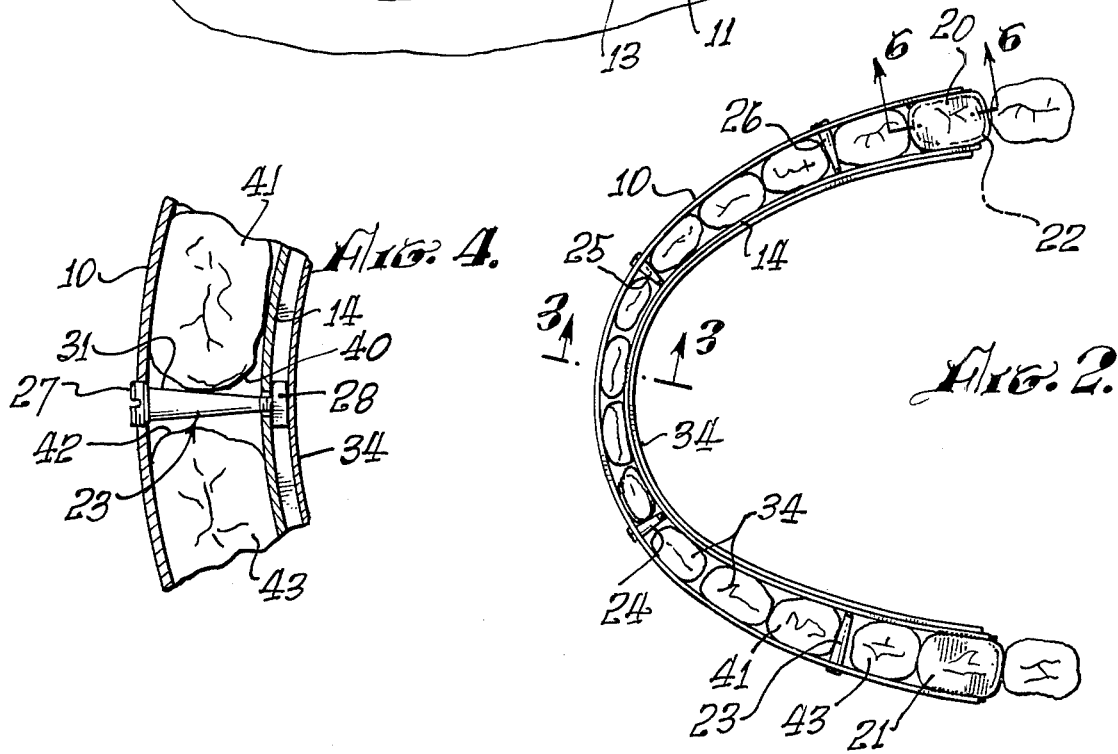
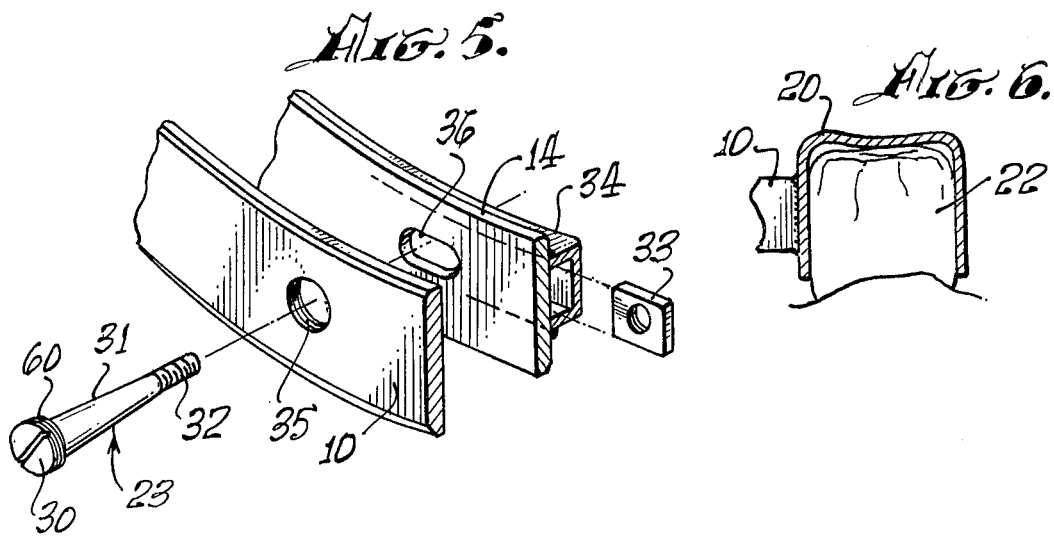

ORTHODONTIC APPLIANCE

BACKGROUND OF THE INVENTION

The field of the invention is orthodontic appliances and more specifically relates to appliances of the type commonly referred to as "braces" useful for straightening or otherwise positioning teeth.

The treatment of tooth irregularities by mechanical means has been known for centuries and it has been estimated that some malocclusion is found in over 90% of the population of the United States. Correction procedures include the removal of one or more teeth and the movement of the remaining teeth to a more desirable location.

Although teeth may be moved with relative ease, it is important that the movement be made in a controlled manner since the teeth will tend to return to their original irregularity if the muscles cannot adapt themselves to the new position. Thus, tooth movement should be made in a highly controlled manner and is typically achieved by metal bands affixed to wires. Typically springs or elastic bands may be used in combination with these bands and wires.

The metal bands and wires of the most commonly used braces suffer from the defect of being relatively unsightly. Since such braces are typically worn by youngsters at a time when their appearance is of great importance, this unsightliness often prevents the acceptance of such devices and leads to the refusal of beneficial treatment. Further, the construction and attachment of prior art devices involves a considerable amount of labor and thus, expense, and requires frequent adjustment by the dentist.

SUMMARY OF THE INVENTION

The present invention is for an orthodontic appliance having an arcuate labial bar shaped to generally conform to the outer surface of a row of teeth and an arcuate lingual bar shaped to position on the inner surface of the same row of teeth. The bars are attached to the teeth and serve to urge the teeth in a desirec direction. The bars may be held in position by screw means to interconnect the same. The use of tapered screws permits the movement of a tooth toward or away from the center of the jaw. The bars may be given a smooth exterior arcuate shape and may be colored to match the color of the teeth and thus, cosmetically, more pleasing than prior art braces. The surface of the bars which contact the teeth may be coated with resilient means to help decrease the need for adjustment. The bars may be attached to a row of teeth by a collar or cap which may be affixed to a molar or other tooth near the extremity of each bar. When the bars are held together by screws, the nut for such screws may be held in a covered channel affixed to the lingual bar to further improve wearer comfort.

BRIEF DESCRIPTION OF THE DRAWINGS

FIG. 1 is a perspective view of a lower jaw having the orthodontic appliance of the present invention affixed thereto.

FIG. 2 is a plan view of the device of FIG. 1.

FIG. 3 is a cross sectional view taken along line 3—3 of FIG. 2.

FIG. 4 is an enlarged plan view of the attachment means of the device of FIG. 1.

FIG. 5 is an enlarged perspective view partly in cross section of the orthodontic appliance of FIG. 1.

FIG. 6 is a cross sectional view taken along line 6—6 of FIG. 2.

DESCRIPTION OF THE PREFERRED EMBODIMENTS

Figure 7:
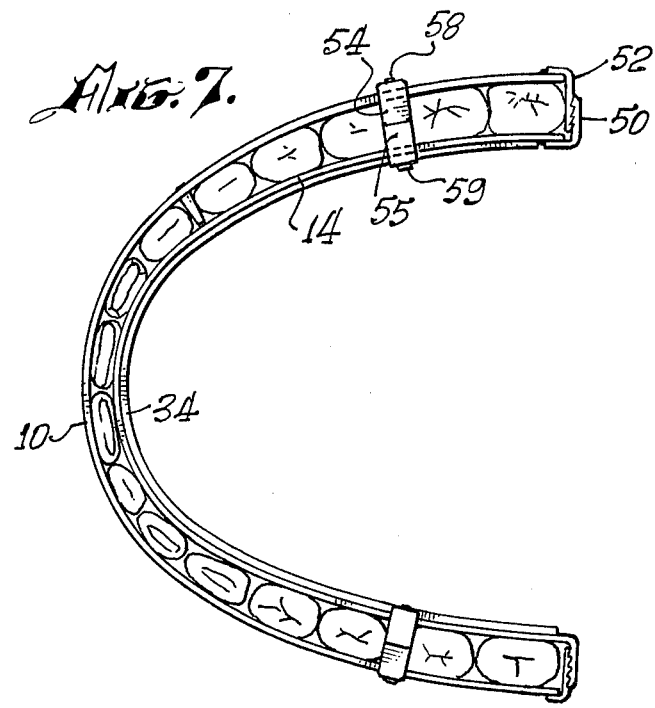
FIG. 7 is a plan view of the orthodontic appliance after installation on a row of teeth.

An orthodontic appliance of the present invention is shown in perspective view in FIG. 1 where a labial bar 10 is positioned on the outer surface of a row of teeth. The labial bar 10 may be formed from any suitable material giving due consideration to corrosion resistance, physical strength and ability to be safely used in the mouth. A commonly used and appropriate material is cast chrome-cobalt.

Bar 10 is welded to a collar 11 which is fitted around molar 12. Other means of attachment such as adhesive, rivets or the like may be used in place of the weld 13.

A lingual bar 14 is positioned along the inner surface of the row of teeth and is welded to collar 15, the welding being indicated by reference character 16. Lingual bar 14 is welded also to the inner surface of collar 11 and labial bar 10 is welded to the outer surface of collar 15 to complete the attachment of the bars. As shown in FIG. 2 caps 20 and 21 may be used in place of collars 11 and 15. Cap 20 is shown in enlarged view in FIG. 6 and is attached to molar 22 in a conventional manner known to those skilled in the art.

Labial bar 10 and lingual bar 14 may be interconnected by one or more screws, rivets or other attachment means. A plurality of screws 23 through 26 are shown in plan view of FIG. 2 and screw 23 is shown in enlarged view in FIG. 4.

It is advantageous that the screw head 27 and nut 28 be covered so that they cause no sharp protrusions which could injure the user. The screw head could be counter sunk or as shown in FIGS. 4 and 5 may be threaded and utilized to cause lateral movement of a desired tooth in a manner described below. As shown in enlarged perspective view in FIG. 5, a tapered screw 23 has a threaded head 30, a tapered shank 31 and a threaded end 32. A nut 33 is inserted into one end of channel 34 which is welded or otherwise affixed to the inner surface of lingual bar 14. While numerous ways may be used to prevent 33 from forming a sharp inner surface, one such means is a covered channel 34 into which a plurality of nuts may be inserted which cooperate with screws 23 through 26. The opening 35 in bar 10 may be threaded as shown in FIG. 5 for a purpose discussed below and when a nut is used opening 36 in lingual bar 14 should not be threaded. Opening 36 may be elongated to facilitate alignment with nut 33.

When a tapered screw is used in combination with a tapered head, the screw nut only can serve to connect labial bar 10 with lingual bar 14 but may also be used to cause a desired movement of teeth in a lateral direction. As shown in FIG. 4 tapered shank 31 contacts the distal surface 40 of bicuspid 41. The bars may also be arranged so that the shank 31 also contacts the mesial surface 42 of molar 43. As shown in FIG. 4 the further insertion of screw 23 will forece bicuspid 41 toward the center line of the jaw. If screw 23 were positioned so that it contacted both the distal surface of bicuspid 41 and the mesial surface of molar 43, the further insertion of screw 23 would force these two teeth away from one another.

Figure 8:
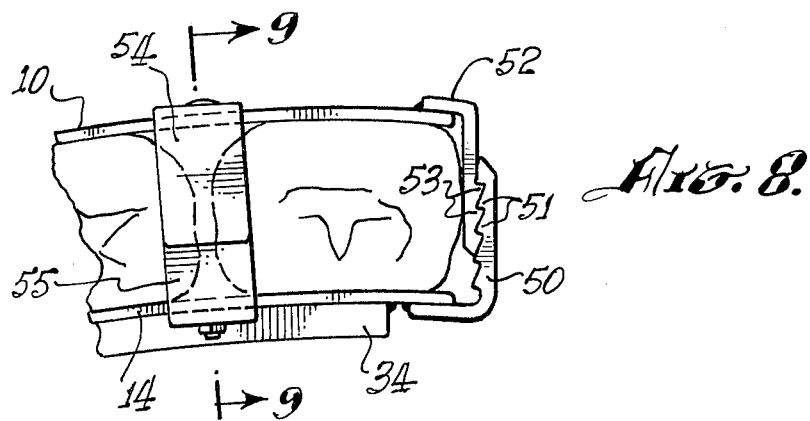
FIG. 8 is an enlarged plan view of the extremity of the device of FIG. 7.
Figure 9:
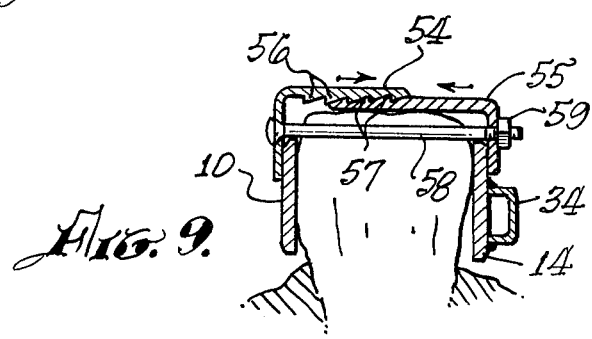
FIG. 9 is a cross sectional view taken along line 9—9 of FIG. 8.

The labial and lingual bars may be connected in a manner shown in FIGS. 7 through 9. An attachment member 50 is affixed t lingual bar 14 and has a plurality of teeth 51. These teeth intermesh with an attachment member 52 which is welded to the labial bar 10 and has a plurality of teeth 53 which intermesh with teeth 51. In this way labial bar 10 and lingual bar 14 can be connected in a relatively inaccessible position behind a molar without the necessity of ready access thereto. An interconnecting member 54 is affixed to member 55. Members 54 and 55 are attached by plurality of teeth 56 and 57 located on the lower surface of member 54 and the upper surface of member 55. These two members are further held together by a screw 58 and nut 59.

Various methods may be used for forming the openings in the labial and lingual bars. The holes may be predrilled and tapped in each bar after the bars are cast and before they are painted or otherwise surfaced. It is also possible to temporarily fill the pre-drilled holes with a plastic or other filler prior to painting or coating. In this way only the necessary openings may be formed by the orthodontist by removing the plastic in the desired pre-drilled openings.

It is useful to incorporate retention beads in those instances where the bars are cast. Such retention beads improve the adhesion of the coating to the surface of the bars. The lost wax process may be used to form the bars in a manner similar to the casting process now widely used in the fabrication of other metallic members used in the mouth. The shape of the arch can be changed with bar benders commonly used by orthodontists in the installation and alteration of conventional braces. Other fabrication processes may be used in place of the last wax process such as extrusion, forging and the like.

While it is not essential that the metal parts be painted or otherwise coated, this does improve the esthetic appearance of them. The bars should be formed or finished so that they do not have sharp edges. The bars may be about 1 mm. in thickness and 3 to 7 mm. in height. The bars should not exceed the height of the teeth. While predrilled bars may be used, it is also possible to use bars which have not been drilled and to have the holes formed according to the particular needs of the user.

The screws may be made from chrome cobalt or from any other material having the requisite strength and compatibility in the human mouth. The screws should be made with varying lengths to permit their use at different points along the arch. The screws should be provided with threads and through the use of a relatively fine thread may become adjustable to a high degree. Sixty threads per inch is a preferred thread size.

The surface of each bar which touches the teeth is preferably coated with a silicone or other resilient liner to improve user comfort and to help urge the teeth in the proper direction. To further improve wearer comfort the bars should be bent in a manner shown in FIG. 3 so that they tend to conform to the outer surface of the teeth which they contact.

The present embodiments of this invention are to be considered in all respects as illustrative of and not restrictive, the scope of the invention being indicated by the appended claims rather than by the foregoing description. All changes which come within the meaning and range of equivalency of the claims therefore are intended to be embraced therein.

What is claimed is:
1. An orthodontic appliance comprising:
an arcuate labial bar shaped to generally comform to the outer surface of a row of teeth; and
an arcuate lingual bar shaped for positioning on the inner surface of said row of teeth and affixed to said labial bar by attachment means, said attachment means being adapted to urge said lingual bar and said labial bar against said row of teeth; and
cooperating ratchet means affixed to the outer extremities of said bars and adapted to pass around the distal surface of a tooth near each extremity of each bar.
2. The appliance of claim 1 wherein said attachment means comprises a screw having an appropriate sized nut positioned on the outer surface of one of said bars.
3. The appliance of claim 2 wherein said nut is positioned in a channel located on the outer surface of said lingual bar.

* * * * *